(12) United States Patent
Mehlberg

(10) Patent No.: US 8,227,366 B2
(45) Date of Patent: Jul. 24, 2012

(54) ALKYLATION SYSTEM INCLUDING A CATALYST REGENERATION ZONE, AND A PROCESS RELATING THERETO

(75) Inventor: Robert L. Mehlberg, Wheaton, IL (US)

(73) Assignee: UOP LLC, Des Plaines, IL (US)

( * ) Notice: Subject to any disclaimer, the term of this patent is extended or adjusted under 35 U.S.C. 154(b) by 444 days.

(21) Appl. No.: 12/476,235

(22) Filed: Jun. 1, 2009

(65) Prior Publication Data

US 2010/0304956 A1  Dec. 2, 2010

(51) Int. Cl.
*B01J 38/56* (2006.01)
(52) U.S. Cl. .......................................................... 502/31
(58) Field of Classification Search .................... None
See application file for complete search history.

(56) References Cited

U.S. PATENT DOCUMENTS

| | | | |
|---|---|---|---|
| 3,879,487 A * | 4/1975 | Vora | 585/712 |
| 4,490,347 A | 12/1984 | Gelblum | |
| 4,503,277 A * | 3/1985 | Himes | 585/455 |
| 4,513,165 A | 4/1985 | Van Pool | |
| 4,850,818 A * | 7/1989 | Kotera | 417/366 |
| 5,098,668 A | 3/1992 | Callen et al. | |
| 5,220,095 A | 6/1993 | Hommeltoft et al. | |
| 5,763,728 A | 6/1998 | Kocal et al. | |
| 6,114,593 A | 9/2000 | Randolph et al. | |
| 6,413,897 B1 | 7/2002 | Randolph et al. | |
| 2003/0130553 A1 | 7/2003 | Randolph et al. | |
| 2008/0139858 A1 | 6/2008 | Cunningham et al. | |
| 2008/0177123 A1* | 7/2008 | Blais et al. | 585/723 |
| 2009/0029846 A1* | 1/2009 | Fitt et al. | 502/31 |

OTHER PUBLICATIONS

Chapin et al., Which Alkylation—HF or H2SO4?, Hydrocarbon Processing, Sep. 1985, vol. 64, No. 9, pp. 67-71.
Gravley, ConocoPhillips Reduced Volatility Alkylation Process (ReVAP), Handbook of Petroleum Refining Processes, 2004, Third Edition, , pp. 1.79-1.90.
Alkylation Catalysts Improve Unit Safety, Hydrocarbon Processing, Dec. 2000, vol. 79, No. 12, p. 33.
Alkylation will use a new acid recovery process, Hydrocarbon Processing/HPI Newsletter, Nov. 1965, Publisher: Gulf Publishing Co., vol. 44, No. 11, p. 14.
Macho et al., Skeletal Isomerisation of n-butenes Present in C4 Pyrolysis Residue Fraction, Applied Catalysis A: General, 2000, vol. 203, No. 1, pp. 5-14.
Parker et al., Sustainable Alternatives: Sulphuric Acid Alkylation & Sulphur-Gas Recovery Options, Hydrocarbon Asia, May/Jun. 2005, vol. 15, No. 3, pp. 36-38.
ReVAP Enhanced Alkylation Solutions, Hydrocarbon Online, 1996-2009, Publisher: Phillips Petroleum—Fuels Technology, p. 1.
Wang, Commercial Test of Acid Fractionation and Regeneration Process in HF Alkylation, Petroleum Refinery Engineering, 2005, vol. 35, No. 10, pp. 18-22.
Wang, Abstract of Commercial Test of Acid Fractionation and Regeneration Process in HF Alkylation, 2005, p. 1.

* cited by examiner

*Primary Examiner* — Melvin C Mayes
*Assistant Examiner* — Stefanie Cohen
(74) *Attorney, Agent, or Firm* — James C Paschall

(57) ABSTRACT

One exemplary embodiment can be an alkylation system including a catalyst regeneration zone. Generally, the catalyst regeneration zone includes first and second columns. The first column can provide an overhead stream having a catalyst and a first hydrocarbon, a side-stream having the catalyst and water, and a bottom stream having a second hydrocarbon. Typically, the second column receives the side-stream as a feed.

20 Claims, 1 Drawing Sheet

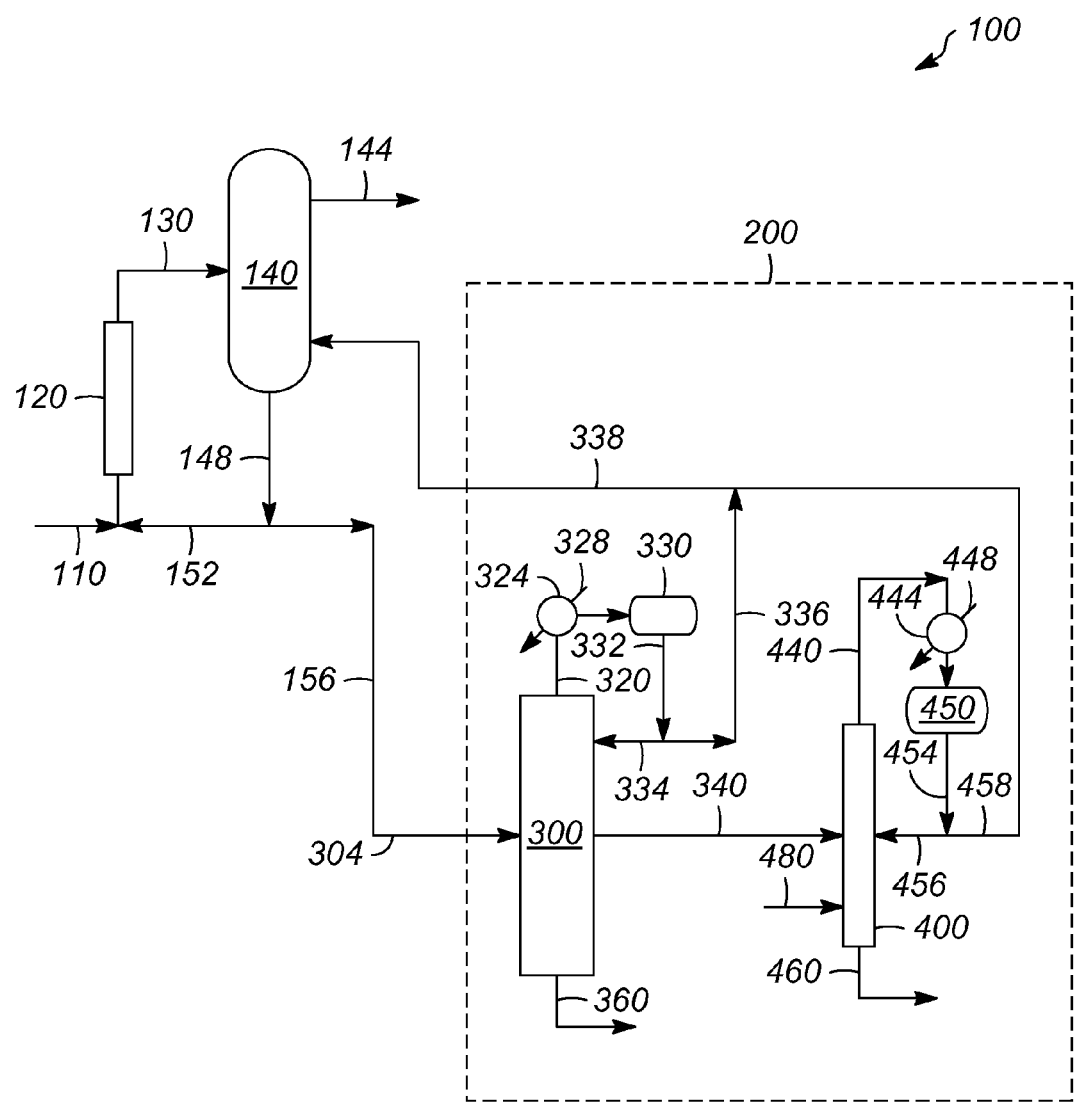

… (1)

ALKYLATION SYSTEM INCLUDING A CATALYST REGENERATION ZONE, AND A PROCESS RELATING THERETO

FIELD OF THE INVENTION

This invention generally relates to an alkylation system including a catalyst regeneration zone, and a process relating thereto.

DESCRIPTION OF THE RELATED ART

An alkylation process can be used to manufacture a high quality octane blend for aviation and motor gasoline. Typically, this product is valued for its relatively low vapor pressure, low sensitivity, and low aromatic content. Usually, the alkylation process reacts a C2-C5 olefin with an isoparaffin, such as an isobutane, in the presence of an acidic catalyst to produce the alkylate product. However, the acidic alkylation process, using e.g., hydrofluoric or sulfuric acid, may have inherent drawbacks including environmental and safety concerns, acid consumption, and sludge disposal. Generally, efforts to develop an inherently safe alkylation process have not resulted in eliminating the use of an acid process. Although acid alkylation catalyst can be highly toxic and corrosive, recognizing the hazards and taking precautions may reduce the hazards associated with handling the acid.

In order to improve the operation of the acid alkylation process, it is generally desired to remove the acid soluble oil (hereinafter may be abbreviated "ASO") from the alkylation acid. Generally, the ASO can be a polymer byproduct typically formed during an alkylation reaction and can include polymers of differing degrees of conjugation. Removal of the ASO is generally desired to preserve the acid concentration for maintaining good alkylation performance. In addition, water may be removed to reduce corrosion as well as to maintain octane product quality. Typically, the acid concentration is maintained at about 88-about 94%, by weight, by the continuous or periodic adding of fresh acid and withdrawing of spent acid with the water content kept in the range of about 0.5-about 1%, by weight.

Unfortunately, the removal of water can result in high acid losses. As an example, utilizing a column with a side draw routed to a condenser can result in eight units of acid lost for each unit of water removed. Moreover, the hydrocarbon phase, enriched in one or more low-boiling sulfur compounds, can be recycled to the acid settler where such compounds can accumulate. Light ASO may be enriched in sulfur compounds. Accumulation of light ASO can reduce acid strength very rapidly, an upset that may be referred to as "acid run-away" often requiring feed removal for recovery. So, it would be desirable to minimize the amount of light ASO in the settler.

Consequently, it would be desirable to provide an acid regeneration zone for an alkylation process that can minimize alkylation catalyst loss and remove light ASO compounds.

SUMMARY OF THE INVENTION

One exemplary embodiment can be an alkylation system including a catalyst regeneration zone. Generally, the catalyst regeneration zone includes first and second columns. The first column can provide an overhead stream having a catalyst and a first hydrocarbon, a side-stream having the catalyst and water, and a bottom stream having a second hydrocarbon. Typically, the second column receives the side-stream as a feed.

Another exemplary embodiment may be a catalyst regeneration zone of an alkylation unit. The catalyst regeneration zone may include a first column and a second column containing a packing communicating with the first column.

Yet another exemplary embodiment can be a process for regenerating an alkylation catalyst. Usually, the process includes providing a mixture comprising the alkylation catalyst and water to a packed column.

The embodiments provided herein can provide a column for removing water without excessive alkylation catalyst losses. Moreover, the additional separation stage can also remove light ASO compounds and prevent such compounds from accumulating within the unit.

DEFINITIONS

As used herein, the term "stream" can be a stream including various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated C1, C2, C3 . . . Cn where "n" represents the number of carbon atoms in the one or more hydrocarbon molecules.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "rich" can mean an amount of at least generally about 30%, preferably about 50%, and optimally about 70%, by mole, of a compound or class of compounds in a stream, a feed, a reflux, or an effluent.

As used herein, the term "substantially" can mean an amount of at least generally about 80%, preferably about 90%, and optimally about 99%, by mole, of a compound or class of compounds in a stream, a feed, a reflux, or an effluent.

As used herein, the term "substantially free" can mean an amount of no more than generally about 10%, preferably about 1%, and optimally about 0.1%, by mole, of a compound or class of compounds in a stream, a feed, a reflux, or an effluent.

As used herein, the term "vapor" can mean at least one of a gas or a dispersion that may include or consist of one or more hydrocarbons.

As used herein, the term "hydrogen fluoride" can include at least one of a hydrogen fluoride or a hydrofluoric acid. Generally, a hydrofluoric acid is a solution of a hydrogen fluoride in water, where the hydrogen fluoride can disassociate and may form ions of $H_3O^+$, $H^+$, $FHF^-$, and $F^-$.

As used herein, the term "acid soluble oil" can include a polymer byproduct typically formed during an alkylation reaction and can include polymers of differing degrees of conjugation and may be abbreviated "ASO". ASO can include light ASO boiling at no more than about 180° C., preferably at about 90-about 150° C., and heavy ASO boiling at least about 150° C., preferably at least about 180° C.

As depicted, process flow lines in the figures can be referred to as lines, feeds, effluents, refluxes, or streams. Particularly, a line can contain one or more feeds, effluents, refluxes, or streams, and one or more feeds, effluents, refluxes, and streams can be contained by a line.

BRIEF DESCRIPTION OF THE DRAWING

FIG. 1 is a schematic depiction of an exemplary alkylation system or unit.

DETAILED DESCRIPTION

Referring to FIG. 1, an exemplary alkylation system or unit 100 can include a riser reactor 120, a settler 140, and a catalyst regeneration zone 200. Typically, the riser reactor 120 may receive a feed 110 and an alkylation catalyst in a line 152.

Usually, the alkylation reaction can include the reaction of an isoparaffin, such as isobutane, with an olefin or other alkylating agent such as propylene, isobutylene, butene-1, butenes-2, and amylenes. Generally, the reaction of an isoparaffin with a C3 or a C4 olefin, such as isobutylene, butene-1, and/or butenes-2, is an example of a preferred reaction involving these specified materials and mixture. Usually, the stream rich in isobutane can at least be partially provided by recycling isobutane from a downstream fractionation zone and include make-up isobutane from one or more other refinery or chemical manufacturing units. Generally, the feed 110 can include a combination of streams, typically a stream including an isoparaffin, and a stream including one or more olefins.

Typically, the alkylation catalyst can include hydrogen fluoride. Generally, the alkylation reaction is carried out with substantial molar excess of isoparaffin:olefin, typically in excess of about 0.5:1, usually about 1:1-about 70:1, preferably about 1:1-about 20:1. Usually, the system or unit 100 can maintain an acid:hydrocarbon volume ratio of about 1:1-about 5:1.

The system or unit 100 may be operated with a volatility reducing agent to improve safety margins in the event of an uncontrolled acid release. The volatility reducing agents normally contemplated are those that may reduce the volatility of the acid alkylation catalyst. The agent may include at least one of an organic sulfone, such as 3-methylsulfolane, 2,4-dimethylsulfolane, and tetramethylenesulfone, which may also be referred to as sulfolane, an ammonia, an amine, such as a lower alkylamine (e.g., methyl to pentyl), a pyridine, an alkylpyridine, a picoline, a melamine, and a hexmethylene-tetramine. Exemplary volatility reducing agents are disclosed, in, e.g., US 2008/0177123 A1.

The riser reactor 120 can provide the reaction effluent 130 to the settler 140. Several phases can form in the settler 140 including a hydrocarbon phase that can be extracted as a hydrocarbon effluent 144 and an acid phase that can be withdrawn through a line 148. Although a riser reactor 120 fed via gravity from the settler 140 is depicted, it should be understood that different reactor and settler combinations can be used, such as a cooler reactor supplied with an alkylation catalyst from a settler via a fluid transfer device, such as a pump. The riser reactor 120 and settler 140 can be operated at any suitable condition. Particularly, the riser reactor 120 can be operated at a pressure of about 440-about 800 kPa and the settler 140 can be operated at a pressure of no more than about 1,500 kPa, typically no more than about 1,100 kPa.

Generally, the hydrocarbon effluent can be provided to one or more columns for separating out an alkylate product as well as recycling an isoparaffin, such as isobutane. The alkylation catalyst in a line 148 can be at least partially spent and a portion can be recycled to the riser reactor 120 while another portion can be sent through a line 156 for regeneration. This alkylation catalyst in a line 156 can be provided as a feed 304 to the catalyst regeneration zone 200. Exemplary settlers, alkylation reactors, and fractionation zones, are disclosed in, e.g., U.S. Pat. No. 5,098,668.

The catalyst regeneration zone 200 can include any suitable number of columns, such as a first column 300 and a second column 400, which are typically distillation columns. The first column 300 can receive the feed 304, which can be at least a portion of at least partially spent alkylation catalyst from the settler 140, and provide an overhead stream 320, a side-stream 340, and a bottom stream 360. Generally, the overhead stream 320 is substantially free of water, ASO, and a volatility reducing agent. The overhead stream 320 can include a first hydrocarbon, such as an isoparaffin, e.g., isobutane, and the alkylation catalyst, can be cooled in a condenser 324 receiving a cooling water stream 328, and can be sent to a receiver 330. A portion of a receiver effluent 332 may be provided as a reflux 334 with another part withdrawn as a regenerated acid and excess first hydrocarbon in a line 336. The regenerated acid in the line 336 can be provided in a line 338 back to the settler 140, or any other suitable location in the circuit between the riser reactor 120 and the settler 140. Generally, the bottom stream 360 can include a volatility reducing agent and a second hydrocarbon, such as an ASO, which can be a heavier molecular weight or heavy ASO.

The side-stream 340 may include the alkylation catalyst, such as hydrogen fluoride, light ASO, and water. Optionally, the side-stream 340 can be only partially condensed to provide another stage or more of separation by, e.g., controlling the cooling. Generally, the side-stream 340 can be provided to the second column 400, which is preferably a packed column. Any suitable packing can be utilized, such as a packing including at least one of a thermoplastic and at least one metal. If the packing includes a thermoplastic, preferably the thermoplastic is a poly(chlorotrifluoroethylene). One exemplary packing is sold under the trade designation KEL-F by Minnesota Mining and Manufacturing Company of Saint Paul, Minn. If the packing includes a metal, preferably the metal includes a nickel alloy. One suitable nickel alloy is an alloy sold under the trade designation MONEL by Huntington Alloys Corporation of Huntington, W.Va. Typically, the nickel alloy can also include copper and optionally iron. The packing can be of any suitable size, such as rings, beads, and/or a mesh. The second column 400 can also receive heat duty in the form of a superheated hydrocarbon stream 480, such as an isobutane, which may strip residual hydrogen fluoride and dissolved isobutane. Usually, the superheated hydrocarbon stream 480 includes at least one compound of the overhead stream 320 of the first column 300. Also, the superheated hydrocarbon stream 480 can include one or more compounds, such as an isoparaffin, e.g. an isobutane, compatible with the feed 110.

The second column 400 may provide an overhead stream 440 and a bottom stream 460. The overhead stream 440 can include an isobutane and an alkylation catalyst and may be substantially free of light ASO and water. The overhead stream 440 can exit the second column 400 and pass through a condenser 444 that can receive a cooling water stream 448. The overhead stream 440 can then pass to a receiver 450. A stream 454 from the receiver 450 may be split into a reflux 456 provided back to the second column 400 and a regenerated acid and/or isobutane stream 458. The stream 458 can be combined with the stream 338 and provided to the settler 140. The bottom stream 460 can include water and/or a light ASO and may be neutralized before recycling or disposal. As such, the use of the columns 300 and 400 can not only remove one or more heavy ASOs in the first column 400, but can remove one or more light ASOs in the second column 400 to prevent the accumulation of the one or more light ASOs in the system 100.

In one preferred embodiment, the overhead stream 440 can have a relatively small volume and be combined with the overhead stream 320. Thus, the condenser 444 and receiver 450 of the second column 400 may be eliminated. A reflux to the second column 400 can be provided by a liquid isobutane or other paraffin.

Thus, the embodiments herein can remove both water and light ASO contaminants with a minimum loss of alkylation catalyst, and may obviate the requirement of using other equipment, such as a condenser, a decanter, and associated piping. Particularly, this arrangement can eliminate condenser tubes that may have short service life in a wet sulfur-rich environment.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. An alkylation process including a regeneration comprising:
   providing an overhead stream from a first column in a catalyst regeneration zone comprising a catalyst and a first hydrocarbon wherein said first overhead stream is substantially free of water;
   a side-stream from said first column comprising the catalyst and water; and
   a bottom stream from said first column comprising a second hydrocarbon; and
   receiving the side-stream as a feed in a second column in said catalyst regeneration zone.

2. The alkylation process according to claim 1, wherein the catalyst comprises a hydrogen fluoride.

3. The alkylation process according to claim 1, wherein the side-stream further comprises a light ASO.

4. The alkylation process according to claim 1, wherein the first hydrocarbon comprises an isoparaffin.

5. The alkylation process according to claim 4, wherein the isoparaffin comprises an isobutane.

6. The alkylation process according to claim 1, wherein the second hydrocarbon comprises an acid soluble oil.

7. The alkylation process according to claim 1, wherein the bottom stream comprises a volatility reducing agent.

8. The alkylation process according to claim 7, wherein the volatility reducing agent comprises at least one of a sulfone, an ammonia, a methylamine, an ethylamine, a propylamine, a butylamine, a pentylamine, a pyridine, an alkylpyridine, a picoline, a melamine, and a hexamethylene-tetramine.

9. The alkylation process according to claim 7, wherein the volatility reducing agent comprises a 1,1-dioxide tetrahydrothiofuran.

10. The alkylation process according to claim 1, wherein the second column contains a packing.

11. The alkylation process according to claim 10, wherein the packing comprises at least one of a thermoplastic and at least one metal.

12. The alkylation process according to claim 11, wherein the packing comprises a thermoplastic, in turn comprising a poly(chlorotrifluoroethylene).

13. The alkylation process according to claim 11, wherein the packing comprises at least one metal, in turn comprising a nickel alloy.

14. The alkylation process according to claim 1, wherein the second column provides an overhead stream comprising at least one of the catalyst and the first hydrocarbon, and a bottom stream comprising water and the second hydrocarbon.

15. The alkylation process according to claim 1, wherein the heat duty for the second column is supplied by a superheated hydrocarbon stream.

16. A catalyst regeneration zone of an alkylation unit, comprising:
   A) a first column; and
   B) a second column containing a packing communicating with the first column, wherein the heat duty for the second column is supplied by a superheated hydrocarbon stream comprising isobutane.

17. A process for regenerating an alkylation catalyst, comprising:
   providing a mixture comprising the alkylation catalyst and water to a packed column wherein a reflux to a second column comprises a paraffin.

18. The process according to claim 17, wherein the alkylation catalyst comprises a hydrogen fluoride.

19. The process according to claim 17, further comprising providing a superheated hydrocarbon stream as heat duty to the packed column.

20. The process according to claim 1, wherein the side-stream comprises a liquid withdrawn from the first column.

* * * * *